United States Patent
Ozaki

(10) Patent No.: US 11,282,600 B2
(45) Date of Patent: Mar. 22, 2022

(54) MEDICAL COMMUNICATION SYSTEM AND MEDICAL DEVICE

(71) Applicant: OLYMPUS CORPORATION, Hachioji (JP)

(72) Inventor: Takashi Ozaki, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 160 days.

(21) Appl. No.: 16/051,830

(22) Filed: Aug. 1, 2018

(65) Prior Publication Data
US 2018/0336965 A1 Nov. 22, 2018

Related U.S. Application Data

(63) Continuation of application No. PCT/JP2016/081762, filed on Oct. 26, 2016.

(30) Foreign Application Priority Data

Feb. 5, 2016 (JP) .............................. JP2016-021325

(51) Int. Cl.
*G16H 30/20* (2018.01)
*A61B 8/12* (2006.01)
(Continued)

(52) U.S. Cl.
CPC ............ *G16H 30/20* (2018.01); *A61B 8/12* (2013.01); *A61B 8/565* (2013.01); *G16H 15/00* (2018.01);
(Continued)

(58) Field of Classification Search
CPC ........ G16H 30/20; G16H 40/67; G16H 15/00; G16H 30/40; G16H 40/60; G16H 80/00;
(Continued)

(56) References Cited

U.S. PATENT DOCUMENTS 8,254,649 B2 * 8/2012 Matsue .................. G16H 30/20
382/128
2006/0106284 A1 5/2006 Shouji et al.
(Continued)

FOREIGN PATENT DOCUMENTS

JP 2004-337503 A 12/2004
JP 2004-344390 A 12/2004
(Continued)

OTHER PUBLICATIONS

I. Balasingham, H. Ihlen, W. Leister, P. Roe and E. Samset, "Communication of Medical Images, Text, and Messages in Inter-Enterprise Systems: A Case Study in Norway," in IEEE Transactions on Information Technology in Biomedicine, vol. 11, No. 1, pp. 7-13, Jan. 2007, doi: 10.1109/TITB.2006.879597. (Year: 2007).*
(Continued)

*Primary Examiner* — Christopher L Gilligan
*Assistant Examiner* — Bennett Stephen Erickson
(74) *Attorney, Agent, or Firm* — Oliff PLC

(57) ABSTRACT

A medical communication system including a first medical device with a memory storing first additional information to be added to first information related to a subject, a DICOM server, and a second medical device storing second additional information to be added to second information. The first medical device having a processor generating DICOM (Digital Imaging and Communication in Medicine)-format data of the first information, a first transmitter/receiver communicating the second information and at least a portion of the second additional information between the first medical device and the second medical device via a network defined by a prescribed protocol different from the DICOM protocol. The processor generates DICOM-format data of the second information based on at least the second additional information. The second transmitter/receiver commu-
(Continued)

nicates generated DICOM-format data of the first information and the second information with the DICOM server via the network defined by the DICOM protocol.

11 Claims, 16 Drawing Sheets

(51) Int. Cl.
| | | |
|---|---|---|
| G16H 40/67 | (2018.01) | |
| G16H 15/00 | (2018.01) | |
| G16H 30/40 | (2018.01) | |
| G16H 40/60 | (2018.01) | |
| G16H 80/00 | (2018.01) | |
| A61B 8/00 | (2006.01) | |
| A61B 5/00 | (2006.01) | |
| A61B 1/00 | (2006.01) | |

(52) U.S. Cl.
CPC ............ *G16H 30/40* (2018.01); *G16H 40/67* (2018.01); *A61B 1/00009* (2013.01); *A61B 1/00011* (2013.01); *A61B 5/0084* (2013.01); *G16H 40/60* (2018.01); *G16H 80/00* (2018.01)

(58) Field of Classification Search
CPC ....... A61B 8/12; A61B 8/565; A61B 1/00009; A61B 1/00011; A61B 5/0084
USPC .......................................................... 705/3
See application file for complete search history.

(56) References Cited

U.S. PATENT DOCUMENTS

| | | | |
|---|---|---|---|
| 2009/0028410 A1 | 1/2009 | Shimazaki | |
| 2010/0036676 A1* | 2/2010 | Safdi | G16H 15/00 705/2 |
| 2011/0193948 A1* | 8/2011 | Amling | A61B 1/00059 348/68 |
| 2014/0259133 A1* | 9/2014 | Alonso Diaz | G16H 10/60 726/6 |
| 2016/0128549 A1* | 5/2016 | Juergens | A61B 1/045 600/112 |
| 2017/0020627 A1* | 1/2017 | Tesar | A61B 90/37 |
| 2017/0258333 A1* | 9/2017 | Shigeta | A61B 5/0084 |
| 2019/0297513 A1* | 9/2019 | Hirayama | H04W 84/18 |

FOREIGN PATENT DOCUMENTS

| | | |
|---|---|---|
| JP | 2007-148660 A | 6/2007 |
| JP | 2009-022626 A | 2/2009 |

OTHER PUBLICATIONS

P. Suapang, S. Yimmun and A. Puditkanawat, "Web-based Medical Image Archiving and Communication System for Teleimaging," 2011 11th International Conference on Control, Automation and Systems, Gyeonggi-do, 2011, pp. 172-177. (Year: 2011).*
Jan. 24, 2017 International Search Report issued in International Patent Application No. PCT/JP2016/081762.
Jan. 24, 2017 Written Opinion issued in International Patent Application No. PCT/JP2016/081762.
Oct. 17, 2017 Office Action issued in Japanese Patent Application No. 2017-547015.

\* cited by examiner

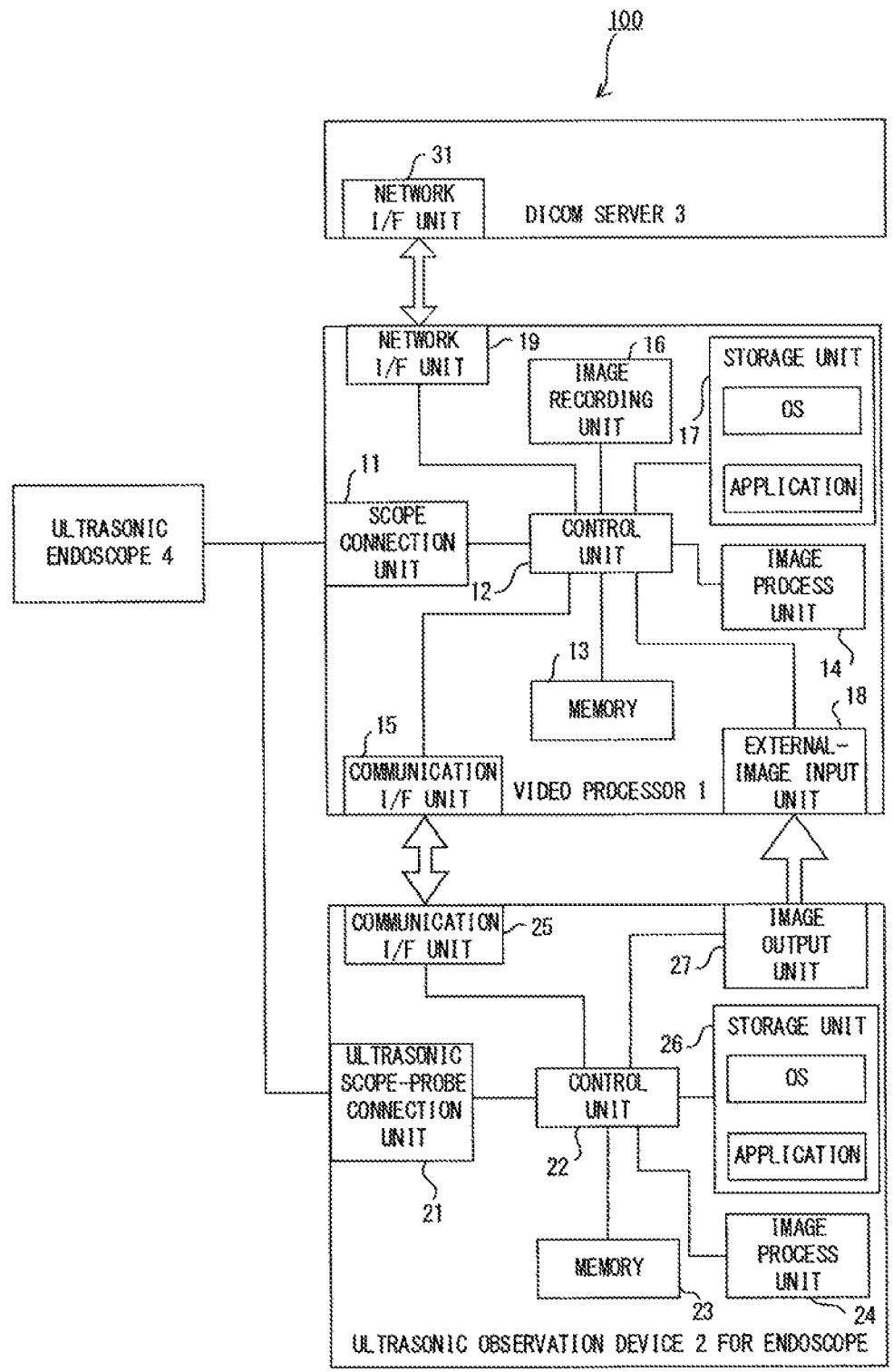
F I G. 1

Storage Attribute List

| Module Name | Attribute Name | Tag | VR | Type | remarks |
|---|---|---|---|---|---|
| Patient Module | Patient's Name | (0010,0010) | PN | 2 | |
| | Patient ID | (0010,0020) | LO | 2 | |
| | Patient's Birth Date | (0010,0030) | DA | 2 | |
| | Patient's Sex | (0010,0040) | CS | 2 | |
| | Patient Comments | (0010,4000) | LT | 3 | |
| | De-identification Method | (0012,0063) | LO | 1C | |
| | De-identification Method Code Sequence | (0012,0064) | SQ | 1C | |
| | >Code Sequence Macro | — | — | — | |
| | Code Value | (0008,0100) | SH | 1C | |
| | Coding Scheme Designator | (0008,0102) | SH | 1C | |
| | Coding Scheme Version | (0008,0103) | SH | 1C | |
| | Code Meaning | (0008,0104) | LO | 1C | |
| | Mapping Resource | (0008,0105) | CS | 1C | |
| | Context Group Version | (0008,0106) | DT | 1C | |
| | Context Group Local Version | (0008,0107) | DT | 1C | |
| | Context Group Extension Creator UID | (0008,010D) | UI | 1C | |

FIG. 3A

Storage Attribute List

| Module Name | Attribute Name | Tag | VR | Type | remarks |
|---|---|---|---|---|---|
| | Study Instance UID | (0020,000D) | UI | 1 | |
| General Study Module | Study Date | (0008,0020) | DA | 2 | |
| | Study Time | (0008,0030) | TM | 2 | |
| | Referring Physician's Name | (0008,0090) | PN | 2 | |
| | Study ID | (0020,0010) | SH | 2 | |
| | Accession Number | (0008,0050) | SH | 2 | |
| | Study Description | (0008,1030) | LO | 3 | |
| Patient Study Module | Patient's Age | (0010,1010) | AS | 3 | |
| | Modality | (0008,0060) | CS | 1 | |
| | Series Instance UID | (0020,000E) | UI | 1 | |
| | Series Number | (0020,0011) | IS | 2 | |
| General Series Module | Laterality | (0020,0060) | CS | 2C | |
| | Series Date | (0008,0021) | DA | 3 | |
| | Series Time | (0008,0031) | TM | 3 | |
| | Patient Position | (0018,5100) | CS | 2C | |
| | Manufacturer | (0008,0070) | LO | 2 | |
| | Station Name | (0008,1010) | SH | 3 | |
| General Equipment Module | Manufacturer's Model Name | (0008,1090) | LO | 3 | |
| | Device Serial Number | (0018,1000) | LO | 3 | |
| | Software Version | (0018,1020) | LO | 3 | |

F I G. 3 B

| Module Name | Attribute Name | Tag | VR | Type | |
|---|---|---|---|---|---|
| General Image Module | Instance Number | (0020,0013) | IS | 2 | |
| | Patient Orientation | (0020,0020) | CS | 2C | |
| | Content Date | (0008,0023) | DA | 2C | |
| | Content Time | (0008,0033) | TM | 2C | |
| | Image Type | (0008,0008) | CS | 3 | A PLURALITY OF VALUES ARE USED FOR IMAGE TYPE ATTRIBUTES SUCH AS IMAGE IDENTIFICATION CHARACTERISTIC "ORIGINAL*PRIMARY". THEY ARE PROVIDED BY THE FOLLOWING METHOD.<br>a. VALUE 1 IS FOR IDENTIFYING PIXEL DATA CHARACTERISTIC: ENUMERATED VALUE FOR PIXEL DATA CHARACTERISTIC: ORIGINAL=ORIGINAL IMAGE IS IDENTIFIED DERIVED=DERIVED IMAGE IS IDENTIFIED<br>b. VALUE 2 IS FOR IDENTIFYING PATIENT EXAMINATION CHARACTERISTIC; ENUMERATED VALUE FOR PATIENT EXAMINATION CHARACTERISTIC: PRIMARY=PRIMARY IMAGE IS IDENTIFIED  SECONDARY=SECONDARY IMAGE IS IDENTIFIED<br>c. VALUE 3 IS FOR IDENTIFYING SPECIALIZATION SPECIFIC TO IMAGE IOD (OPTIONAL) |
| | Burned In Annotation | (0028,0301) | CS | 3 | COLOR-BURNING NOTE INDICATES WHETHER IMAGE INCLUDES ALREADY-COLOR-BURNT NOTE THAT IS ENOUGH TO IDENTIFY DATE AT WHICH PATIENT AND IMAGE WERE COLLECTED. ENUMERATED: YES NO |
| | Lossy Image Compression | (0028,2110) | CS | 3 | |

FIG. 3C

| Module Name | Attribute Name | Tag | VR | Type |
|---|---|---|---|---|
| | Samples Per Pixel | (0028,0002) | US | 1 |
| | Photometric Interpretation | (0028,0004) | CS | 1 |
| | Rows | (0028,0010) | US | 1 |
| | Columns | (0028,0011) | US | 1 |
| | Bits Allocated | (0028,0100) | US | 1 |
| | Bits Stored | (0028,0101) | US | 1 |
| | High Bit | (0028,0102) | US | 1 |
| | Pixel Representation | (0028,0103) | US | 1 |
| Image Pixel Module | Pixel Data | (7FE0,0010) | OW/OB | 1C |
| | Planar Configuration | (0028,0006) | US | 1C |
| | Pixel Aspect Ratio | (0028,0034) | IS | 1C |
| | Red Palette Color Lookup Table Descriptor | (0028,1101) | US/SS | 1C |
| | Green Palette Color Lookup Table Descriptor | (0028,1102) | US/SS | 1C |
| | Blue Palette Color Lookup Table Descriptor | (0028,1103) | US/SS | 1C |
| | Red Palette Color Lookup Table Data | (0028,1201) | OW | 1C |
| | Green Palette Color Lookup Table Data | (0028,1202) | OW | 1C |
| | Blue Palette Color Lookup Table Data | (0028,1203) | OW | 1C |

FIG. 3D

| Module Name | Attribute Name | Tag | VR | Type | (*1) |
|---|---|---|---|---|---|
| US Region Calibration Module | Sequence of Ultrasound Regions | (0018,6011) | SQ | 1 | ULTRASONIC RANGE SEQUENCE DEFINES SEQUENCE OF ULTRASONIC RANGE. SEQUENCE MAY INCLUDE ONE OR MORE ITEMS |
| | >Region Location Min x0 | (0018,6018) | UL | 1 | BORDER OF RECTANGLE SPECIFYING POSITIONS OF REGION x0, y0, x1, y1 UPPER LEFT CORNER OF ENTIRE IMAGE IS REPRESENTED BY x=0, y=0, |
| | >Region Location Min y0 | (0018,601A) | UL | 1 | BORDER OF RECTANGLE SPECIFYING POSITIONS OF REGION x0, y0, x1, y1 UPPER LEFT CORNER OF ENTIRE IMAGE IS REPRESENTED BY x=0, y=0, |
| | >Region Location Max x1 | (0018,601C) | UL | 1 | BORDER OF RECTANGLE SPECIFYING POSITIONS OF REGION x0, y0, x1, y1 UPPER LEFT CORNER OF ENTIRE IMAGE IS REPRESENTED BY x=0, y=0, |
| | >Region Location Max y1 | (0018,601E) | UL | 1 | BORDER OF RECTANGLE SPECIFYING POSITIONS OF REGION x0, y0, x1, y1 UPPER LEFT CORNER OF ENTIRE IMAGE IS REPRESENTED BY x=0, y=0, |

FIG. 3E

| Module Name | Attribute Name | Tag | VR | Type | |
|---|---|---|---|---|---|
| US Region Calibration Module | >Physical Units X Direction | (0018,6024) | US | 1 | PHYSICAL UNIT OF DIMENSION OF REGION<br>VALUE MEANING<br>0000H DOES NOT EXIST OR IS NOT APPLIED<br>0001H %<br>0002H dB<br>0003H cm<br>0004H seconds<br>0005H hertz (seconds-1)<br>0006H dB/seconds<br>0007H cm/sec<br>0008H cm2<br>0009H cm2/sec<br>000AH cm3<br>000BH cm3/sec |
| | >Physical Units Y Direction | (0018,6026) | US | 1 | PHYSICAL UNIT OF DIMENSION OF REGION<br>VALUE MEANING<br>0000H DOES NOT EXIST OR IS NOT APPLIED<br>0001H %<br>0002H dB<br>0003H cm<br>0004H seconds<br>0005H hertz (seconds-1)<br>0006H dB/seconds<br>0007H cm/sec<br>0008H cm2<br>0009H cm2/sec<br>000AH cm3<br>000BH cm3/sec |
| | >Physical Delta X | (0018,602C) | FD | 1 | INCREMENT IN PHYSICAL VALUE FOR POSITIVE X-PIXEL INCREMENT UNIT IS SPECIFIED IN PHYSICAL UNIT DATA ELEMENT |
| | >Physical Delta Y | (0018,602E) | FD | 1 | INCREMENT IN PHYSICAL VALUE FOR POSITIVE Y-PIXEL INCREMENT UNIT IS SPECIFIED IN PHYSICAL UNIT DATA ELEMENT |
| | >Reference Pixel x0 | (0018,6020) | SL | 3 | THIS COORDINATE PAIR x0, y0 DEFINE POSITION OF VIRTUAL "REFERENCE" PIXEL |
| | >Reference Pixel y0 | (0018,6022) | SL | 3 | THIS COORDINATE PAIR x0, y0 DEFINE POSITION OF VIRTUAL "REFERENCE" PIXEL |
| | >Region Spatial Format | (0018,6012) | US | 1 | |
| | >Region Data Type | (0018,6014) | US | 1 | |
| | >Region Flags | (0018,6016) | US | 1 | |

(*2)

F I G. 3 F

| Module Name | Attribute Name | Tag | VR | Type | |
|---|---|---|---|---|---|
| | Samples per Pixel | (0028,0002) | US | 1 | NUMBER OF SAMPLES (PLANES) IN THIS IMAGE |
| | Photometric Interpretation | (0028,0004) | CS | 1 | PHOTOMETRIC MEASUREMENT INTERPRETATION SAMPLE VALUE PER PIXEL CLEARLY DESCRIBE INTERPRETATION INTENDED BY PIXEL DATA |
| | Bits Allocated | (0028,0100) | US | 1 | NUMBER OF BITS ASSIGNED TO EACH PIXEL SAMPLE |
| | Bits Stored | (0028,0101) | US | 1 | NUMBER OF BITS STORED FOR EACH PIXEL SAMPLE |
| | High Bit | (0028,0102) | US | 1 | MOST SIGNIFICANT BIT FOR PIXEL SAMPLE DATA |
| | Planar Configuration | (0028,0006) | US | 1C | INDICATES WHETHER PIXEL DATA IS TRANSMITTED BY COLOR IN UNITS OF SURFACE OR BY COLOR IN UNITS OF PIXEL NECESSARY WHEN SAMPLE (0028,0002) PER PIXEL HAS VALUE GREATER THAN 1 |
| US Image Module | Pixel Representation | (0028,0103) | US | 1 | DATA EXPRESSION OF PIXEL SAMPLE PIXEL EXPRESSION (0028,0103) FOR ULTRASONIC IMAGE CLEARLY DESCRIBES THE USE OF FOLLOWING ENUMERATED VALUE 0000H =UNSIGNED INTEGER |
| | Frame Increment Pointer | (0028,0009) | AT | 1C | INCLUDES DATA ELEMENT TAG OF ATTRIBUTE USED AS FRAME INCREMENT IN PLURAL-FRAME PIXEL DATA (SEE C.7.6.6) NECESSARY WHEN NUMBER OF FRAMES HAS BEEN TRANSMITTED |
| | Image Type | (0008,0008) | CS | 3 | IMAGE IDENTIFICATION CHARACTERISTIC |
| | Lossy Image Compression | (0028,2110) | CS | 2 | CLEARLY DESCRIBES WHETHER IMAGE EXPERIENCED LOSSY COMPRESSION |
| | Number of Stages | (0008,2124) | IS | 2C | NUMBER OF STAGES IN THIS PROTOCOL NECESSARY WHEN IMAGES WERE COLLECTED IN STAGE PROTOCOL |
| | Number of Views in Stage | (0008,212A) | IS | 2C | NUMBER OF VIEWS IN THIS STAGE NECESSARY WHEN IMAGES WERE COLLECTED IN STAGE PROTOCOL |
| | R Wave Time Vector | (0018,5060) | FL | 3 | |

F I G. 3 G

| Module Name | Attribute Name | Tag | VR | Type | |
|---|---|---|---|---|---|
| US Image Module | Ultrasound Color Data Present | (0028,0014) | US | 3 | THIS ELEMENT INDICATES WHETHER SOME ULTRASONIC COLOR DATA EXISTS IN IMAGE ENUMERATED VALUE: 00=ULTRASONIC COLOR DATA DOES NOT EXIST IN IMAGE, 01=ULTRASONIC COLOR DATA EXISTS IN IMAGE |
| | Stage Name | (0008,2120) | SH | 3 | STAGE IS SPECIFIC-TIME SLICE OF PROTOCOL FOR WHICH SETS OF IMAGES IN IT WERE COLLECTED THE NAME CAN BE IN FREE-FORM TEXT RECOMMENDED TEXTS FOR STRESS-ECHO-STAGE NAME ARE PRE-EXERCISE POST-EXERCISE PEAK-EXERCISE RECOVERY BASELINE, LOW DOSE, PEAK DOSE |
| | Stage Code Sequence | (0040,000A) | SQ | 3 | ITEM SEQUENCE THAT DESCRIBES IMPLEMENTED ULTRASONIC PROTOCOL STAGE |
| | Stage Number | (0008,2122) | IS | 3 | NUMBER FOR IDENTIFYING STAGE    STAGE NUMBER STARTS WITH "1" |
| | View Name | (0008,2127) | SH | 3 | WHEN SETS OF IMAGES WERE COLLECTED, VIEW IS PARTICULAR COMBINATION OF POSITION AND DIRECTION IMAGES ARE COLLECTED IN THE SAME VIEW OF DIFFERENT STAGE FOR PURPOSE OF COMPARISON |
| | View Number | (0008,2128) | IS | 3 | NUMBER FOR IDENTIFYING VIEW    VIEW NUMBER STARTS WITH "1" |
| | Number of Event Timers | (0008,2129) | IS | 3 | NUMBER OF EVENT TIMERS USED FOR COLLECTING PLURAL-FRAME IMAGE |
| | Event Elapsed Time(s) | (0008,2130) | DS | 3 | ARRAY OF VALUES RELATED TO RESPECTIVE EVENT TIMERS, UNIT IS msec |
| | Event Timer Name(s) | (0008,2132) | LO | 3 | NAME FOR IDENTIFYING EVENT TIMER |
| | View Code Sequence | (0054,0220) | SQ | 3 | SEQUENCE DESCRIBING PROJECTION OF ANATOMICAL REGION OF INTEREST TO IMAGE RECEIVER |
| | Acquisition Datetime | (0008,002A) | DT | 1C | TIME AND DATE AT WHICH DATA FROM WHICH THIS IMAGE WAS MADE STARTED NECESSARY WHEN MODALITY (0008, 0060)=IVUS    MAY EXIST IN OTHER CASES |

FIG. 3H

| Module Name | Attribute Name | Tag | VR | Type | |
|---|---|---|---|---|---|
| US Image Module | Trigger Time | (0018,1060) | DS | 3 | TIME INTERVAL BETWEEN STARTING POINT OF R WAVE AND START OF IMPORTING OF DATA. UNIT IS msec |
| | Nominal Interval | (0018,1062) | IS | 3 | AVERAGE R-R TIME INTERVAL USED FOR THESE PIECES OF DATA. UNIT IS msec |
| | Beat Rejection Flag | (0018,1080) | CS | 3 | PULSE LENGTH SORTING WAS APPLIED. ENUMERATED VALUE: Y=YES N=NO |
| | Low R-R Value | (0018,1081) | IS | 3 | R-R INTERVAL LOWER LIMIT FOR PULSE REMOVAL. UNIT msec |
| | High R-R Value | (0018,1082) | IS | 3 | R-R INTERVAL UPPER LIMIT FOR PULSE REMOVAL. UNIT msec |
| | Heart Rate | (0018,1088) | IS | 3 | NUMBER OF PULSES PER MINUTE |
| | IVUS Acquisition | (0018,3100) | CS | 3 | IVUS COLLECTION. DEFINED WORD: MOTOR_PULLBACK MANUAL_PULLBACK SELECTIVE GATED_PULLBACK NECESSARY WHEN MODALITY (0008,0060)=IVUS |
| | IVUS Pullback Rate | (0018,3101) | DS | 3 | NECESSARY WHEN IVUS COLLECTION (0018,3100) VALUE IS MOTOR_PULLBACK SPECIFIED BY UNIT mm/sec |
| | IVUS Gated Rate | (0018,3102) | DS | 3 | NECESSARY WHEN IVUS COLLECTION (0018,3100) VALUE IS GATED_PULLBACK SPECIFIED BY UNIT mm/beat |
| | IVUS Pullback Start Frame Number | (0018,3103) | IS | 3 | NECESSARY WHEN IVUS COLLECTION (0018,3100) VALUE IS MOTOR_PULLBACK OR GATED_PULLBACK |
| | IVUS Pullback Stop Frame Number | (0018,3104) | IS | 3 | NECESSARY WHEN IVUS COLLECTION (0018,3100) VALUE IS MOTOR_PULLBACK OR GATED_PULLBACK |
| | Lesion Number | (0018,3105) | IS | 1C | IDENTIFIER OF LESION OF INTEREST TAKEN AS IMAGE IN CURRENT SOP INSTANCE EACH LESION HAS SPECIFIC VALUE INTEGER IDENTIFIER IN EXAMINATION |
| | Output Power | (0018,5000) | SH | 3 | CHARACTER STRINGS DESCRIPTION OF MANUFACTURER DEFINITION AT ULTRASONIC OUTPUT LEVEL USED FOR GENERATING GIVEN IMAGE DATA MAY BE EXPRESSED BY DB, %, W/cm2, etc. |

F I G. 3 1

| Module Name | Attribute Name | Tag | VR | Type | |
|---|---|---|---|---|---|
| US Image Module | Transducer Data | (0018,5010) | LO | 3 | CODE OR DESCRIPTION OF MANUFACTURER DEFINITION OF USED ULTRASONIC PROBE |
| | Transducer Type | (0018,6031) | CS | 3 | PROBE TYPE DEFINED WORD: SECTOR_PHASED SECTOR_MECH SECTOR_ANNULAR LINEAR CURVED LINEAR SINGLE CRYSTAL SPLIT XTAL CWD IV_PHASED IV_ROT XTAL IV_ROT MIRROR ENDOCAV_PA ENDOCAV_MECH ENDOCAV_AA ENDOCAV_LINEAR VECTOR_PHASED |
| | Focus Depth | (0018,5012) | DS | 3 | FOCAL DEPTH DEPTH FROM SURFACE OF PROBE OF MANUFACTURER DEFINITION BEAM FOCUS USED FOR IMAGE: UNIT cm |
| | Processing Function | (0018,5020) | LO | 3 | PROCESS FUNCTION DESCRIPTION OF MANUFACTURER DEFINITION OF PROCESS OF ECHO INFORMATION DATA MAY INCLUDE GAIN (INITIAL, OVERALL, TGC, DYNAMIC RANGE, etc.) PRE-PROCESSING, POST-PROCESSING, DOPPLER PROCESSING PARAMETER, CODE OR DESCRIPTION SUCH AS FOR EXAMPLE CUTOFF FILTER |
| | Mechanical Index | (0018,5022) | DS | 3 | MECHANICAL INDEX |
| | Bone Thermal Index | (0018,5024) | DS | 3 | BONE HEAT INDEX |
| | Cranial Thermal Index | (0018,5026) | DS | 3 | CRANIUM HEAT INDEX |
| | Soft Tissue Thermal Index | (0018,5027) | DS | 3 | SOFT TISSUE HEAT INDEX |
| | Soft Tissue-focus Thermal Index | (0018,5028) | DS | 3 | SOFT TISSUE FOCUS HEAT INDEX |
| | Soft Tissue-surface Thermal Index | (0018,5029) | DS | 3 | SOFT TISSUE SURFACE HEAT INDEX |
| | Depth of Scan Field | (0018,5050) | IS | 3 | IMAGE DISPLAYED FROM PROBE SURFACE, DEPTH TO DEEPEST PART INCLUDED IN FIELD OF VIEW UNIT: mm |
| | Overlay Subtype | (60xx,0045) | LO | 3 | DEFINED WORD FOR IDENTIFYING PURPOSE INTENDED BY ROI OVERLAY TYPE |

F I G. 3 J

| Module Name | Attribute Name | Tag | VR | Type | |
|---|---|---|---|---|---|
| | SOP Class UID | (0008,0016) | UI | 1 | |
| | SOP Instance UID | (0008,0018) | UI | 1 | |
| | Specific Character set | (0008,0005) | CS | 1C | |
| | Instance Creation Date | (0008,0012) | DA | 3 | DATE AT WHICH SOP INSTANCE WAS GENERATED |
| | Instance Creation Time | (0008,0013) | TM | 3 | TIME AT WHICH SOP STANCE WAS GENERATED |
| | Instance Creator UID | (0008,0014) | UI | 3 | UNIQUELY IDENTIFY DEVICE THAT GENERATED SOP INSTANCE |
| SOP Common Module | Encrypted Attributes Sequence | (0400,0500) | SQ | 1C | |
| | >Encrypted Content Transfer Syntax UID | (0400,0510) | UI | 1 | |
| | >Encrypted Content | (0400,0520) | OB | 1 | |
| | HL7 Structured Document Reference Sequence | (0040,A390) | SQ | 1C | |
| | >Referenced SOP Class UID | (0008,1150) | UI | 1 | |
| | >Referenced SOP Instance UID | (0008,1155) | UI | 1 | |
| | >HL7 Instance Identifier | (0040,E001) | ST | 1 | |

FIG. 3K

| Module Name | Attribute Name | Tag | VR | Type | |
|---|---|---|---|---|---|
| VOI LUT | Window Center | (0028,1050) | DS | 1C | CENTER OF WINDOW FOR DISPLAY |
| | Photometric Interpretation | (0028,0004) | CS | 1C | PHOTOMETRIC MEASUREMENT INTERPRETATION |
| Cine Module | Frame Time | (0018,1063) | DS | 1C | NOMINAL TIME FOR EACH FRAME: UNIT msec |
| | Frame Time Vector | (0018,1065) | DS | 1C | ARRAY INCLUDING INCREMENT OF ACTUAL TIME (UNIT msec) BETWEEN FRAMES FOR PLURAL-FRAME IMAGE |
| Multi-frame | Number of Frames | (0028,0008) | IS | 1 | NUMBER OF FRAMES IN PLURAL-FRAME IMAGE |
| | Frame Increment Pointer | (0028,0009) | AT | 1 | INCLUDES DATA ELEMENT TAG OF ATTRIBUTE USED AS FRAME INCREMENT IN PLURAL-FRAME PIXEL DATA |

F I G. 3 L

MEDICAL COMMUNICATION SYSTEM AND MEDICAL DEVICE

CROSS-REFERENCE TO RELATED APPLICATIONS

This application is based upon and claims the benefit of priority of the prior Japanese Patent Application No. 2016-021325, filed Feb. 5, 2016, the entire contents of which are incorporated herein by reference.

This is a Continuation Application of PCT Application No. PCT/JP2016/081762, filed Oct. 26, 2016, which was not published under PCT Article 21 (2) in English.

FIELD

The present exemplary embodiment is related to a medical communication system that includes a plurality of medical devices and a server for storing a medical image, and that transmits and receives the medical image between the medical device and the server, the medical devices obtaining the medical image through an examination etc., and is related to the medical device. The present exemplary embodiment is related particularly to a medical communication system and a medical device that are compatible with the DICOM (Digital Imaging and Communication in Medicine) standard.

BACKGROUND

In recent years, systems compatible with the DICOM standard tend to be used for managing medical images that have been obtained by picking up images of the examination subject through the use of a medical device such as an endoscopic device etc. in medical scenes. A system compatible with the DICOM standard generates DICOM-format data from a medical image obtained by a medical device, and stores the data in a DICOM-compatible server.

In some conventional use cases, one endoscopic examination uses a plurality of image-pickup devices such as an ultrasonic endoscope etc. in addition to an ordinary endoscope. A use case of using such a plurality of image-pickup devices will hereinafter be referred to also as a use case of multi modality. A system compatible with the DICOM standard that can respond to such a use case is also being discussed and has been made public (Japanese Laid-open Patent Publication No. 2009-022626 for example).

Currently, there is a limitation that only one modality can be used for one examination that is conducted through communications with a DICOM server on a network compatible with a DICOM protocol.

The DICOM standard defines information that is added to image data of each of the endoscopic image and the ultrasonic image.

SUMMARY

According to an aspect of the present exemplary embodiment, a medical communication system includes a first medical device including: a memory storing first additional information to be added to first information related to a subject, a processor programmed to generate DICOM (Digital Imaging and Communication in Medicine)-format data of the first information, a first transmitter/receiver, and a second transmitter/receiver. The medical communication system further includes a DICOM server configured to communicate with the first medical device via a network defined by a DICOM protocol, and a second medical device configured to store second additional information to be added to second information related to the subject. The first transmitter/receiver is configured to communicate the second information and at least a portion of the second additional information stored in the second medical device between the first medical device and the second medical device via a network defined by a prescribed protocol different from the DICOM protocol. The processor is programmed to generate DICOM-format data of the second information based on at least the second information and the second additional information received from the second medical device via the first transmitter/receiver. The second transmitter/receiver is configured to communicate generated DICOM-format data of the first information and generated DICOM-format data of the second information with the DICOM server via the network defined by the DICOM protocol.

BRIEF DESCRIPTION OF DRAWINGS

FIG. 1 illustrates a configuration of a medical system according to the exemplary embodiment;

FIG. 3A exemplifies information necessary for generating DICOM-format ultrasonic image data;

FIG. 3B exemplifies information necessary for generating DICOM-format ultrasonic image data;

FIG. 3C exemplifies information necessary for generating DICOM-format ultrasonic image data;

FIG. 3D exemplifies information necessary for generating DICOM-format ultrasonic image data;

FIG. 3E exemplifies information necessary for generating DICOM-format ultrasonic image data;

FIG. 3F exemplifies information necessary for generating DICOM-format ultrasonic image data;

FIG. 3G exemplifies information necessary for generating DICOM-format ultrasonic image data;

FIG. 3H exemplifies information necessary for generating DICOM-format ultrasonic image data;

FIG. 3I exemplifies information necessary for generating DICOM-format ultrasonic image data;

FIG. 3J exemplifies information necessary for generating DICOM-format ultrasonic image data;

FIG. 3K exemplifies information necessary for generating DICOM-format ultrasonic image data;

FIG. 3L exemplifies information necessary for generating DICOM-format ultrasonic image data;

DESCRIPTION OF EXEMPLARY EMBODIMENTS

Figure 2:
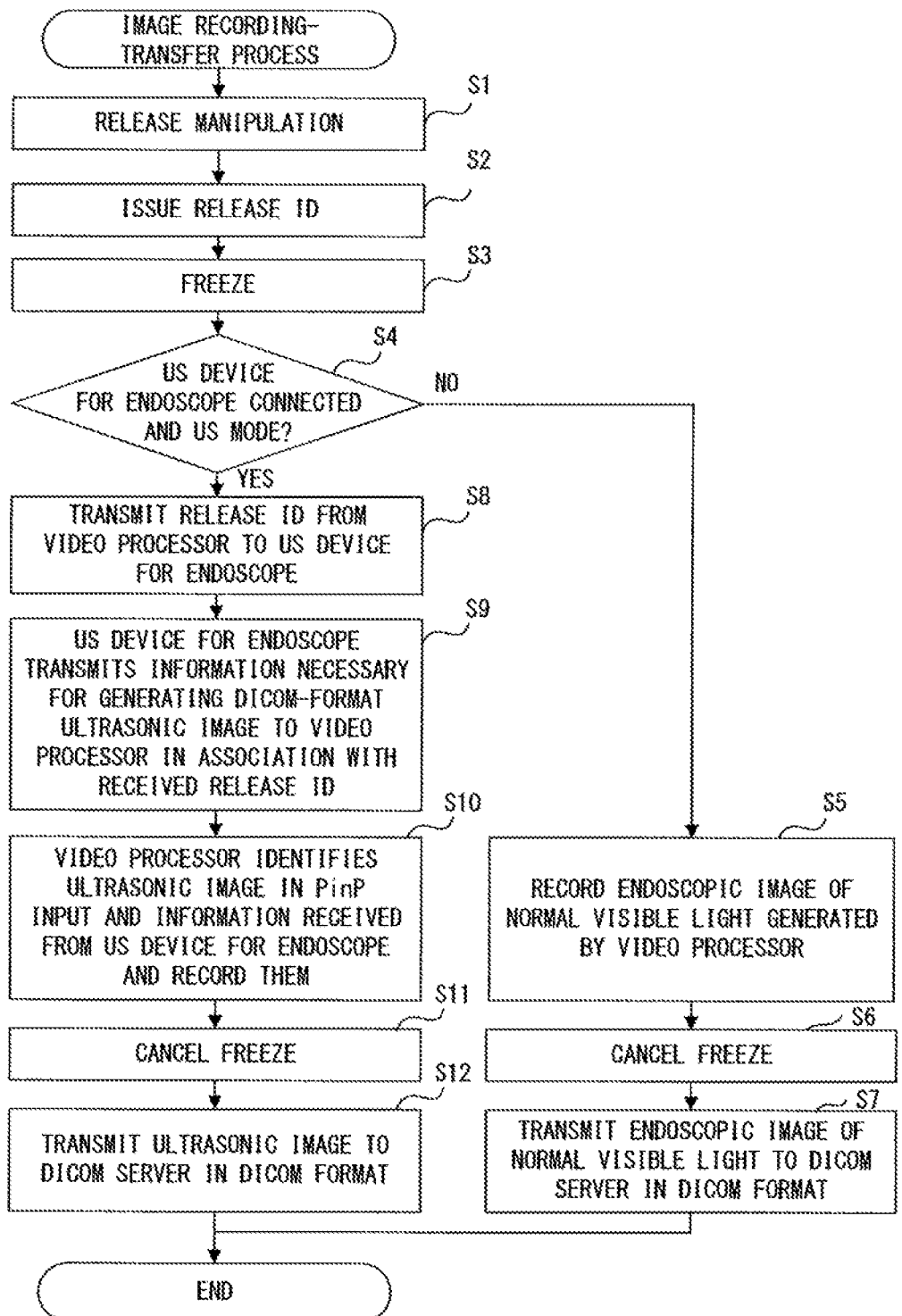
FIG. 2 is a flowchart explaining a process in which a medical system according to the exemplary embodiment records an image and transfers an image to a DICOM server.

Hereinafter, detailed explanations will be given for the exemplary embodiments by referring to the drawings.

FIG. 1 illustrates a configuration of a medical system according to the present exemplary embodiment. A medical system 100 illustrated in FIG. 1 includes a video processor 1, an ultrasonic observation device 2 for an endoscope, an ultrasonic endoscope 4, and a DICOM server 3. Hereinafter, the ultrasonic observation device 2 for an endoscope will be referred to as the ultrasonic observation device 2. The medical system 100 performs a necessary process on an image signal obtained from the examination subject through the ultrasonic endoscope 4, and thereby generates data having a DICOM-format data structure so as to store this data in the DICOM server 3.

The video processor 1 includes a scope connection unit 11, a control unit 12, an image process unit 14, an image recording unit 16, a storage unit 17, a memory 13, a communication interface unit 15, an external-image input unit 18, and a network interface unit 19. In FIG. 1 and the subsequent figures, the communication interface unit 15 and the external-image input unit 18 will be referred to as the communication I/F unit 15 and the network I/F unit 19, respectively. The video processor 1 generates DICOM-format endoscopic image data and DICOM-format ultrasonic image data in the medical system 100 illustrated in FIG. 1.

In the video processor 1, the scope connection unit 11 serves as a connection interface unit with the ultrasonic endoscope 4, and receives an image signal that is input from the ultrasonic endoscope 4. While FIG. 1 illustrates the ultrasonic endoscope 4, the scope of the exemplary embodiment is not limited to this, and an ordinary endoscope and an ultrasonic probe may be used instead of this.

The control unit 12 controls the respective units constituting the video processor 1, and also controls connected devices, such as the ultrasonic endoscope 4 etc., in relation to endoscopic examinations. When receiving a release signal from the ultrasonic endoscope 4 via the scope connection unit 11, the control unit 12 performs a process in which the respective units are controlled in accordance with the observation mode of the ultrasonic endoscope 4 so as to make the respective units generate DICOM-format image data. The control unit 12 also performs a process of transmitting the generated data to the DICOM server 3. Such processes will be described later specifically and in detail.

The image process unit 14 performs a necessary process on the input image signal so as to obtain DICOM-format endoscopic image data in the normal mode as the above observation mode. Note that the normal mode is a mode in which an endoscope is used for observations. Information necessary for generating DICOM-format endoscopic image data is stored in the memory 13. The image recording unit 16 temporarily records the obtained image data. The video processor 1 communicates with the DICOM server 3 in a DICOM protocol, and the image data recorded in the image recording unit 16 is transmitted to the DICOM server 3 via the network interface unit 19.

The external-image input unit 18 receives the input of an image signal that received a necessary process through the ultrasonic observation device 2 in the ultrasonic mode as the above observation mode. Note that the ultrasonic mode is a mode in which an ultrasonic observation device is used for observations. In addition to this, information necessary for obtaining DICOM-format image data is obtained for the ultrasonic image from the ultrasonic observation device 2 by performing communications with the ultrasonic observation device 2 via the communication I/F unit 15 in a prescribed protocol that is different from a DICOM protocol in the ultrasonic mode in the present exemplary embodiment.

The storage unit 17 stores the operating system (OS), an application, and etc. of the video processor 1. The control unit 12 reads the OS and an application from the storage unit 17 to develop and execute them, thereby controls the respective units of the video processor 1 and the system, generates DICOM-format image data according to the present exemplary embodiment, transmits the generated image data to the DICOM server 3, and performs other processes.

The ultrasonic observation device 2 includes an ultrasonic scope-probe connection unit 21, a control unit 22, an image process unit 24, a storage unit 26, a memory 23, a communication interface unit 25, and an image output unit 27. In FIG. 1 and the subsequent figures, the communication interface unit 25 will be referred to as the communication I/F unit 25. When the ultrasonic mode is set as the observation mode for the endoscopic examination, the ultrasonic observation device 2 performs a necessary process on an image signal input from the ultrasonic endoscope 4, and outputs the signal to the video processor 1. In addition to this, the ultrasonic observation device 2 according to the present exemplary embodiment transmits, to the video processor 1, information necessary for generating DICOM-format ultrasonic image data.

The ultrasonic scope-probe connection unit 21 serves as a connection interface unit with the ultrasonic endoscope 4, and receives an image signal input from the ultrasonic endoscope 4.

The control unit 22 controls the respective units constituting the ultrasonic observation device 2, and, when receiving an image signal from the ultrasonic endoscope 4 via the ultrasonic scope-probe connection unit 21, controls the respective units such as the image process unit 24 etc. to make them generate ultrasonic image data.

As described above, the image process unit 24 performs a necessary process on the image signal input via the ultrasonic scope-probe connection unit 21, and generates ultrasonic image data. In order to generate DICOM-format image data in the video processor 1, the generated image data and its corresponding prescribed information are transmitted to the video processor respectively via the image output unit 27 and the communication I/F unit 25. This will be explained later in detail.

The storage unit 26 stores the operating system (OS), an application, and etc. of the ultrasonic observation device 2. The control unit 22 reads the OS and an application from the storage unit 26 to develop and execute them, and thereby controls the respective units of the ultrasonic observation device 2. The control unit 22 according to the present exemplary embodiment performs for example a transmission process in which image data and information necessary for the video processor 1 to generate DICOM-format ultrasonic image data are transmitted to the video processor 1. Information necessary for generating DICOM-format ultrasonic image data is stored in the memory 23.

As described above, the video processor 1 generates DICOM-format data from an image that is obtained on the basis of whether the normal mode or the ultrasonic mode is set as the observation mode in the endoscopic examination, and transmits the generated image to the DICOM server 3. The DICOM server 3 stores data received via a network interface unit 31. Note in FIG. 1 that the network interface unit 31 is referred to as the network I/F unit 31.

When the ultrasonic mode is set as the observation mode, the video processor 1 receives the necessary information and the image data that received the image process from the ultrasonic observation device 2, and generates DICOM-format ultrasonic image data on the basis of this. This will be explained specifically by referring to the flowcharts etc.

FIG. 2 is a flowchart explaining a process in which the medical system 100 according to the present exemplary embodiment records an image and transfers an image to the DICOM server 3.

The video processor 1, when starting one endoscopic examination, generates identification information such as an ID (Identification) for identifying an examination, sets information for identifying the modality to be used for the examination, and holds these pieces of information in the memory 13. "Modality" herein refers to a medical device. In the configuration illustrated in FIG. 1, "endoscope" is set as the modality to be used.

When the information for identifying the examination and the modality to be used are set, the examination starts. The user such as a doctor etc. thereafter observes the inside of the body cavity of the examination subject by using the ultrasonic endoscope 4 while appropriately switching the observation mode between the normal mode and the ultrasonic mode. When finding a spot etc. that may involve a lesion, the user manipulates a manipulation button etc. at the user's hand. A release signal is issued from the ultrasonic endoscope 4 in response to the manipulation, and is input to the video processor 1. In step S1, the control unit 12 of the video processor 1 detects the release manipulation on the basis of the signal.

In step S2, the control unit 12 of the video processor 1 issues a release ID for identifying a release. Thereafter, the control unit 12 detects, through a freeze signal input from the ultrasonic endoscope 4, that the user performed a freeze manipulation in step S3, and the process proceeds to the determination in step S4.

In step S4, the control unit 12 determines whether the ultrasonic observation device 2 is connected to the medical system 100 and the ultrasonic mode is set as the observation mode. When the ultrasonic observation device 2 is connected to the medical system 100 and the observation mode is the ultrasonic mode, the process proceeds to step S8, and in the other cases, the process proceeds to step S5.

In step S5 and the subsequent steps, the DICOM-format endoscopic image is recorded and is transferred to the DICOM server 3. Specifically, the control unit 12 of the video processor 1 in step S5 first generates DICOM-format endoscopic image data from the data of an endoscopic image of normal visible light obtained by performing a necessary process in the image process unit 14 and from information held in the memory 13, and records the data in the image recording unit 16. When the control unit 12 detects the cancellation of the release in step S6, the control unit 12 reads the data of the DICOM-format endoscopic image from the image recording unit 16 in step S17, and transmits the data to the DICOM server 3. Upon the termination of the transmission process, the series of the processes in FIG. 2 is terminated. The processes of recording and transferring an endoscopic image are similar to those in the conventional techniques in which the modality to be used is endoscope.

In step S8 and the subsequent steps, the DICOM-format ultrasonic image is recorded and transferred to the DICOM server 3. Specifically, the control unit 12 of the video processor 1 in step S8 first transmits the release ID issued in step S2 to the ultrasonic observation device 2 via the communication I/F unit 15. When the control unit 22 of the ultrasonic observation device 2 receives the release ID via the communication I/F unit 25 in step S9, the control unit 22 reads the information necessary for generating the DICOM-format ultrasonic image data from the memory 23. The control unit 22 associates the read information with the received release ID, and transmits them to the video processor 1 via the communication I/F unit 25.

FIG. 3A through FIG. 3L exemplify information necessary for generating DICOM-format ultrasonic image data.

The DICOM standard defines the data structure of information that is to be added to image data, and the video processor 1 adds the defined pieces of information (metadata) respectively to the endoscopic image and the ultrasonic image in accordance with this definition, and thereby generates DICOM-format image data.

Note that FIG. 3A through FIG. 3L illustrate the difference between the endoscopic image data and the ultrasonic image data of the DICOM-format image data in a shaded manner. The items that are not shaded are similar to information that is added to the data of the endoscopic image, and the video processor 1 utilizes the information held in the memory 13 belonging to the video processor 1.

The explanation returns to FIG. 2, in which when the communication I/F unit 25 of the ultrasonic observation device 2 transmits the information shaded in FIG. 3A through FIG. 3L in step S9, the video processor 1 receives the information via the communication I/F unit 15. In addition to this, the ultrasonic observation device 2 transmits, to the video processor 1 and from the image output unit 27, ultrasonic image data obtained by performing a necessary process in the image process unit 24. The video processor 1 receives the image data via the external-image input unit 18.

In order to reduce the communication amount, the ultrasonic observation device 2 in step S9 transmits only the portion different from the DICOM-format endoscopic image (the items shaded in FIG. 3A through FIG. 3L) to the video processor 1 via the communication I/F unit 25 as described above. However, the scope of the present exemplary embodiment is not limited to this example, and for example all the items in FIG. 3A through FIG. 3L may be transmitted.

The control unit 12 of the video processor 1 in step S10 uses the ultrasonic image in the PinP (Picture in Picture) input received via the external-image input unit 18 and at least the information received via the communication I/F unit 15 to generate DICOM-format ultrasonic image data. As described above, the DICOM-format ultrasonic image data is generated by adding the metadata illustrated in FIG. 3A through FIG. 3L to image data or pixel data. In the example, information not held in the video processor 1 is obtained from the ultrasonic observation device 2. The generated DICOM-format ultrasonic image data is recorded in the image recording unit 16 in association with the release ID issued in step S2.

In step S11 and step S12, processes similar to those in step S6 and step S7 are performed, respectively. In other words, when the control unit 12 detects the cancellation of the freeze in step S11, the control unit 12 reads the DICOM-format image data from the image recording unit 16 and transmits the data to the DICOM server 3. Upon the termination of the transmission process, the series of the processes in FIG. 2 is terminated.

As described above, after the information for identifying an examination and the modality to be used have been set to start one examination, the series of the processes illustrated in FIG. 2 is performed each time the user thereafter performs a release manipulation. In other words, the medical system 100 according to the present exemplary embodiment makes it possible to generate the DICOM-format image data for each of the endoscopic image and the ultrasonic image in accordance with the observation mode employed when a release manipulation is performed in one examination and to register the image data in the DICOM server 3.

As described above, the medical system 100 according to the present exemplary embodiment can generate DICOM-format image data for an endoscopic image or ultrasonic image obtained in accordance with the observation mode in a use case of multi modality and register the data in the DICOM server 3. While according to the DICOM standard, one modality is set for one examination, for a different modality, necessary information is obtained from that different modality side. In the above example, one modality is endoscopic, and the different modality is ultrasonic device. Using the obtained information makes it possible to generate DICOM-format data also for an image obtained with a modality that is not set as a modality to be used.

Data related to an endoscopic examination registered in the DICOM server 3 is used for purposes including the generation of a report after the examination. The ultrasonic image has been registered in the DICOM server 3 in the DICOM format similarly to the endoscopic image, enabling the user to utilize the information, illustrated in FIG. 3A through FIG. 3L in a hatched manner, that is added to the ultrasonic image upon the generation of the report.

For example, the module "US Region Calibration Module" illustrated in FIG. 3E and FIG. 3F includes x0, y0, x1, and y1, which represent the positional coordinates of the vertexes of the ultrasonic image expressed in a rectangle, respectively as the attribute names ("Region Location Min x0" of Attribute name etc.) ((*1) in FIG. 3E). Physical units in the x and y directions ("Physical Units X (Y) Direction" of Attribute Name), and the increment thereof ("Physical Delta X (Y)" of Attribute Name), and the reference positional coordinates x0, y0 ("Reference Pixel x0 (y0)" of Attribute Name) are also included ((*2) in FIG. 3F). These pieces of information enable the user to for example identify a spot that may involve a lesion etc. in an image so as to generate a report or to do other tasks.

While FIG. 1 illustrates a configuration in which a DICOM-format image obtained in one examination in accordance with the observation mode is generated in the video processor 1, the scope of the present exemplary embodiment is not limited to this example. For example, a configuration is also possible in which the ultrasonic observation device 2 performs the above process. In that case, the ultrasonic observation device 2 receives a release manipulation and a freeze manipulation performed by the user, and issues a release ID to transmit it to the video processor 1. The video processor 1 that received the release ID reads, from the memory 13 belonging to itself, information necessary for generating a DICOM-format endoscopic image, and transmits it in association with the release ID. On the basis of the release ID, the ultrasonic observation device 2 associates image data to be received from the video processor 1 with information necessary for generating a DICOM-format image to be received from the video processor 1, and generates the data of a DICOM-format endoscopic image so as to transmit the data to the DICOM server 3. This configuration also achieves similar effects to those achieved by the configuration illustrated in FIG. 2.

It is also possible to configure a medical system in such a manner that three or more medical devices each can obtain an image and generate a DICOM-format image. In that case, the medical system is configured so that a plurality of types of medical devices can communicate a release ID and image data with a medical device that is connected to the DICOM server 3 and that generates and transfers a DICOM-format image. For example, when the video processor 1 is connected to the DICOM server 3 and generates and transfers a DICOM-format image, the video processor 1 issues a release ID in accordance with a release manipulation and transmits the release ID to the medical device in accordance with the observation mode. Operations performed in the medical device that received a release ID and operations performed in the video processor 1 after receiving necessary information in association with the release ID are similar to those in the case of the above configuration with two medical devices. As described above, configurations with three or more medical devices achieve effects similar to those achieved by the configuration with two medical devices illustrated in FIG. 2.

The above exemplary embodiment generates a DICOM-format image as a still image. The present exemplary embodiment is different in generating a DICOM-format video image.

Explanations will hereinafter be given for the medical system according to the present exemplary embodiment centering on points different from the exemplary embodiment.

Figure 4:
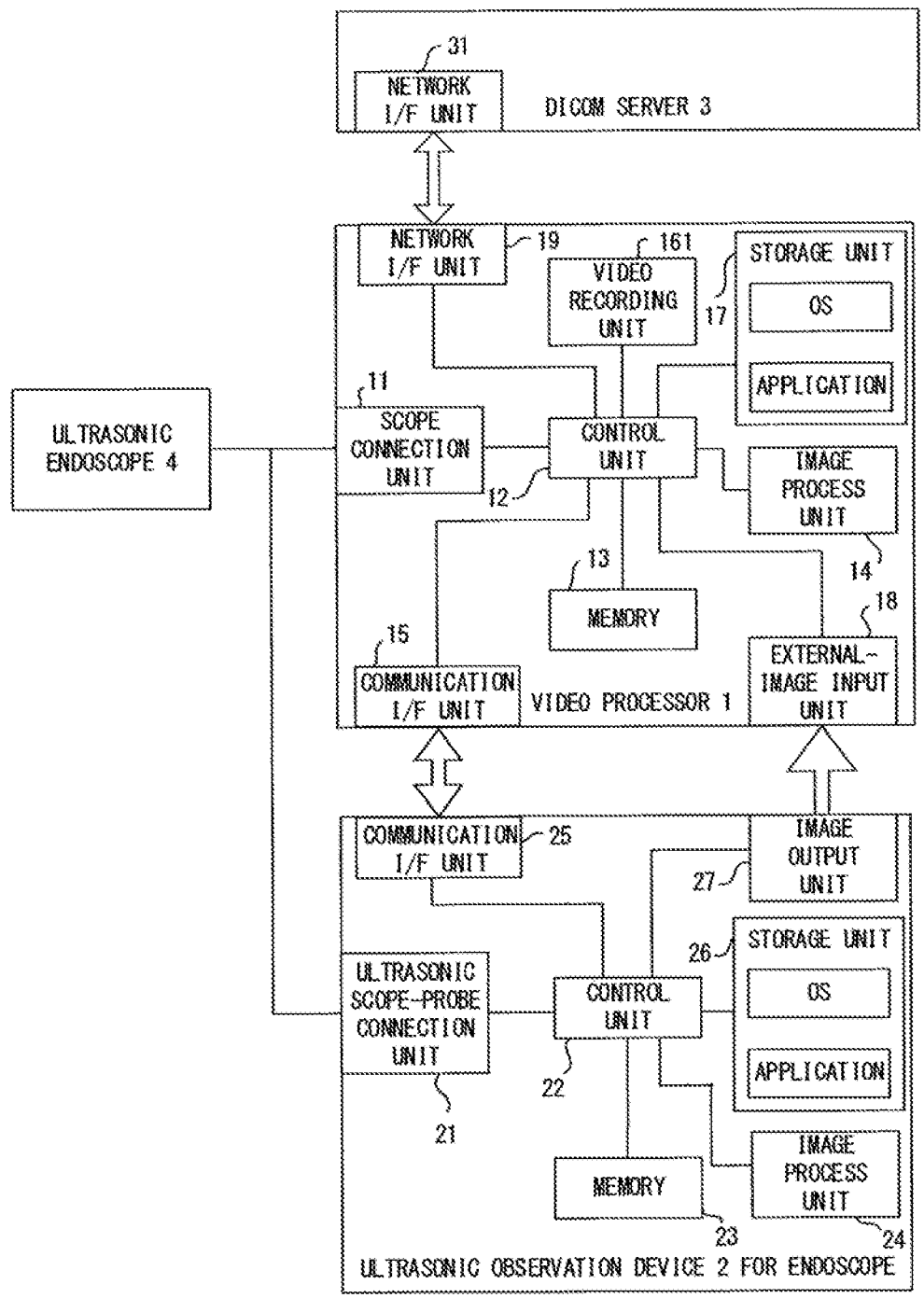
FIG. 4 illustrates a configuration of a medical system according to the exemplary embodiment.

FIG. 4 illustrates a configuration of the medical system 100 according to the present exemplary embodiment. While the video processor 1 illustrated in FIG. 1 makes the image recording unit 16 record a generated DICOM-format image as illustrated in the configuration diagram of FIG. 1 for the exemplary embodiment, a DICOM-format video image is recorded in a video recording unit 161 in FIG. 4, which is a different point.

According to the medical system 100 of the present exemplary embodiment, an endoscopic video is imported in the normal mode as the above observation mode, and an ultrasonic video is imported in the ultrasonic mode as the above observation mode. In accordance with the set observation mode, DICOM-format video data is generated for the corresponding modality, and the generated DICOM-format video data is registered in the DICOM server 3. Specific explanations will be given for this method by referring to flowcharts.

Figure 5:
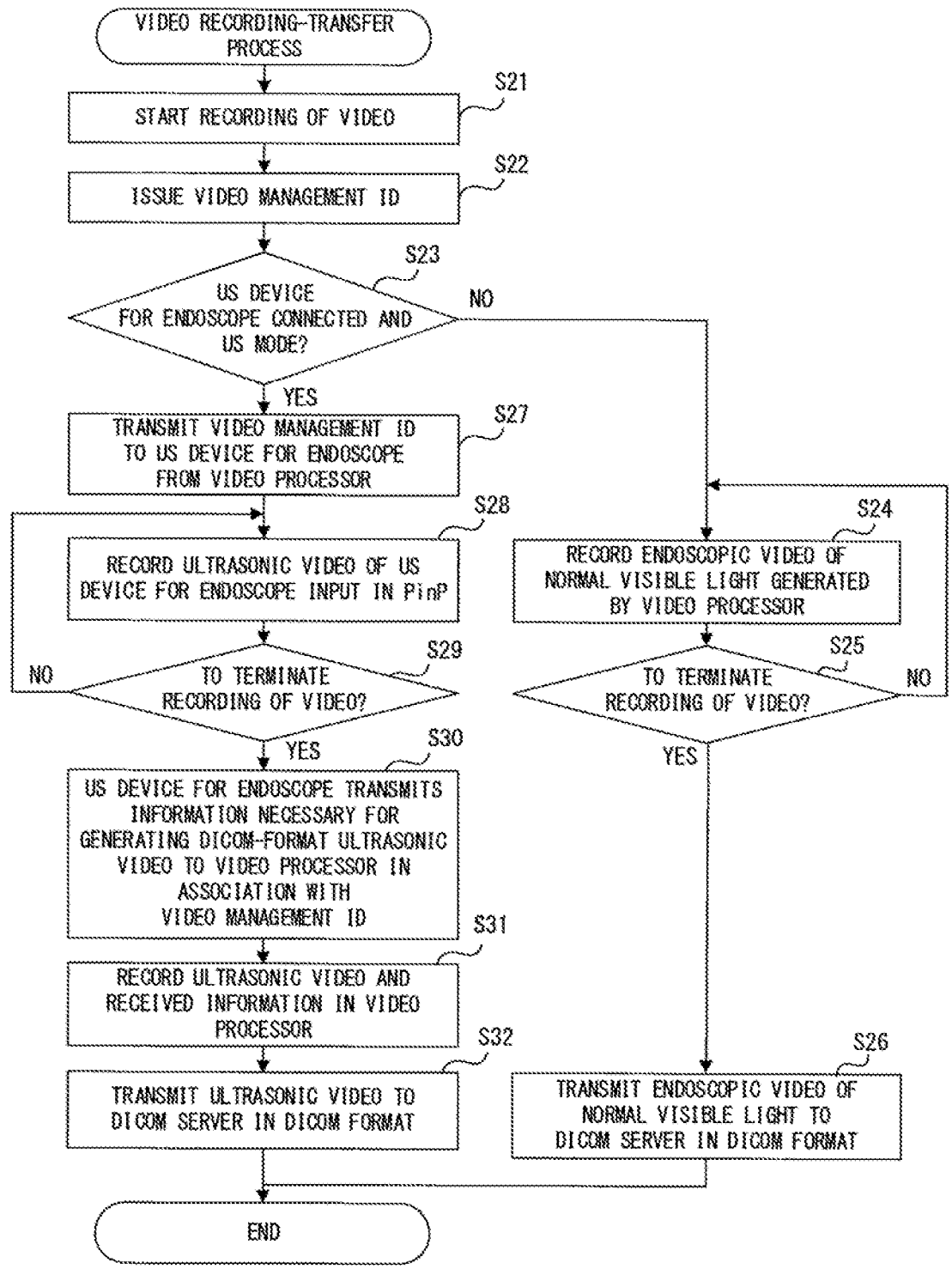
FIG. 5 is a flowchart explaining a process in which the medical system according to the exemplary embodiment records a video image and transfers a video image to a DICOM server.

FIG. 5 is a flowchart explaining a process in which the medical system 100 according to the present exemplary embodiment records a video image and transfers a video image to the DICOM server 3.

Similarly to the case in FIG. 2 where a still image is recorded and transferred, the video processor 1, when starting one endoscopic examination, generates identification information for identifying an examination, sets information for identifying the modality to be used for the examination, and holds these pieces of information in the memory 13. In the configuration illustrated in FIG. 4, "endoscope" is set as the modality to be used.

When the information for identifying the examination and the modality to be used are set, the examination starts. The user thereafter observes the inside of the body cavity of the examination subject by using the ultrasonic endoscope 4 while appropriately switching the observation mode between the normal mode and the ultrasonic mode. When finding a spot etc. that may involve a lesion, the user manipulates a manipulation button etc. at the user's hand in order to instruct that the recording of a video image start. A signal instructing that the recording of a video image start is issued from the ultrasonic endoscope 4 in response to the manipulation, and is input to the video processor 1. In step S21, the signal makes the control unit 12 of the video processor 1 detect the instruction to start the recording of the video image.

In step S22, the control unit 12 of the video processor 1 issues a management ID for managing the video. The process then proceeds to the determination in step S23.

The determination in step S23 is similar to the determination in step S4 illustrated in FIG. 2. When the ultrasonic observation device 2 is connected to the medical system 100 and the observation mode is the ultrasonic mode, the process proceeds to step S27, and in the other cases, the process proceeds to step S24.

In step S24 and the subsequent steps, the DICOM-format endoscopic video is recorded and is transferred to the DICOM server 3. Specifically, the control unit 12 of the video processor 1 in step S24 first generates DICOM-format endoscopic video data from the data of an endoscopic video of normal visible light obtained by performing a necessary process in the image process unit 14 and from information held in the memory 13, and records the data in the video recording unit 161. In step S25, the control unit 12 determines whether a signal instructing that the recording of the video be terminated has been received from the ultrasonic endoscope 4, and continues the process of recording the DICOM-format endoscopic video in step S24 until receiving such a signal. When such a signal is received, the process proceeds to step S26, where the control unit 12 reads the data of the DICOM-format endoscopic video from the video recording unit 161 so as to transmit the data to the DICOM server 3. Upon the termination of the transmission process, the series of the processes in FIG. 5 is terminated. Similarly to FIG. 2, the processes of recording and transferring an endoscopic image are similar to those in the conventional techniques in which the modality to be used is endoscope.

By contrast, in step S27 and the subsequent steps, the DICOM-format ultrasonic video is recorded and transferred to the DICOM server 3. Specifically, the control unit 12 of the video processor 1 in step S27 first transmits the management ID issued in step S22 to the ultrasonic observation device 2 via the communication I/F unit 15. When receiving the management ID via the communication I/F unit 25, the control unit 22 of the ultrasonic observation device 2 holds the ID in the memory 23. In addition to this, the control unit 22 of the ultrasonic observation device 2 transmits, to the video processor 1 and from the image output unit 27, ultrasonic video data obtained by performing a necessary process in the image process unit 24, and the video processor 1 receives the video data via the external-image input unit 18.

In step S28, the control unit 12 of the video processor 1 records, in the video recording unit 161, the ultrasonic video in the PinP input that has been received via the external-image input unit 18. Then, the control unit 12 in step S29 determines whether a signal instructing that the recording of the video be terminated has been received from the ultrasonic endoscope 4, and continues the process of recording ultrasonic video in the video recording unit 161 in step S28 until receiving such a signal. When receiving such a signal, the process proceeds to step S30.

In step S30, the control unit 22 of the ultrasonic observation device 2 reads, from the memory 23, information necessary for generating DICOM-format ultrasonic video data in the video processor 1. The control unit 22 associates the read information with the received management ID, and transmits them to the video processor 1 via the communication I/F unit 25. The video processor 1 receives the information via the communication I/F unit 15.

In step S31, the control unit 12 of the video processor 1 associates the data of the video recorded in the video recording unit 161 in step S28 with the information received in step S30, generates the data of DICOM-format ultrasonic video, and again records this in the video recording unit 161. In step S32, the control unit 12 reads the data of the DICOM-format ultrasonic video from the video recording unit 161, and transmits it to the DICOM server 3. Upon the termination of the transmission process, the series of the processes in FIG. 5 is terminated.

As described above, effects similar to those achieved by the exemplary embodiment can be achieved also by treating video data as in the medical system 100 of the present exemplary embodiment. The present exemplary embodiment is similar to the exemplary embodiment also in that the ultrasonic observation device 2 obtains necessary information from the video processor 1 so as to generate DICOM-format endoscopic video and it can be applied to a medical system with three or more medical devices.

The above respective embodiments make it possible to generate DICOM-format data in accordance with each modality even in a use case of multi modality and register the data in a DICOM server under the current DICOM standard.

The present exemplary embodiment is not limited to the above embodiments as they are, but can be embodied by changing constituents in the implementation without departing from the spirit thereof. It is also possible to form various exemplary embodiments by an appropriate combination of a plurality of constituents disclosed in the above embodiments. For example, it is possible to appropriately combine all the constituents that are disclosed in the embodiments. It is further possible to appropriately combine constituents disclosed in different embodiments. Of course, these various changes and applications are possible without departing from the spirit of the exemplary embodiment.

What is claimed is:
1. A medical communication system comprising:
an endoscopic device including:
   a memory storing first additional information to be added to first information related to a subject, the first information being an endoscope image,
   a processor programmed to generate DICOM (Digital Imaging and Communication in Medicine)-format data of the first information,
   a first transmitter/receiver, and
   a second transmitter/receiver;
a DICOM server configured to communicate with the first medical device via a network defined by a DICOM protocol; and
an ultrasonic observation device configured to store second additional information to be added to second information related to the subject, the second information being an ultrasonic image, wherein:
   the first transmitter/receiver is configured to communicate the second information and at least a portion of the second additional information stored in the ultrasonic observation device between the endoscopic device and the ultrasonic observation device via a network defined by a prescribed protocol different from the DICOM protocol;
   the processor is programmed to generate DICOM-format data of the second information based on at least the second information and the second additional information received from the ultrasonic observation device via the first transmitter/receiver;
   the ultrasonic observation device (i) compares the first information to the second information, and determines a segment of data of the second information that is different than the first information based on the comparison between the first information and the second information, and (ii) transmits only the segment of data of the second information and the second additional information to the first transmitter/ receiver of the endoscopic device using the prescribed protocol different from the DICOM protocol; and the second transmitter/receiver is configured to communicate generated DICOM-format data of the first information and generated DICOM-format data of the second information with the DICOM server via the network defined by the DICOM protocol.

2. The medical communication system according to claim 1, wherein:

the processor is programmed to generate DICOM-format data of both the first information and the second information in one examination for the endoscopic device, and the second transmitter/receiver transmits, to the DICOM server, the generated DICOM-format data of both the first information and the second information in the one examination.

3. The medical communication system according to claim 2, wherein the first transmitter/receiver receives identification information identifying the second information, and communicates with the ultrasonic observation device to obtain the second information and information indicating at least a difference between the second additional information and the first additional information.

4. The medical communication system according to claim 3, wherein the ultrasonic observation device transmits, to the endoscopic device, at least the difference in association with the identification information.

5. The medical communication system according to claim 4, wherein the processor generates the DICOM-format data of the second information based on the identification information, the second information, and at least information received via the first transmitter/receiver, the DICOM-format data of the second information being generated by adding metadata defined by a DICOM protocol to the second information.

6. The medical communication system according to claim 1, wherein:

the first information includes an endoscopic video generated by the endoscopic device, and the second information includes an ultrasonic endoscopic video generated by the ultrasonic observation device for an endoscope.

7. The medical communication system according to claim 1, wherein:

the ultrasonic observation device includes an ultrasonic endoscope configured to issue a signal upon detecting the subject by using the ultrasonic endoscope;

the processor is programmed to issue identification information after receiving the signal from the ultrasonic endoscope; and the ultrasonic observation device is configured to associate the identification information with the second information.

8. The medical communication system according to claim 7, wherein the signal issued by the ultrasonic endoscope is a release signal in response to manipulation of an input device, and the issued identification information is a release identification identifying the manipulation of the input device.

9. The medical communication system according to claim 7, wherein the signal issued by the ultrasonic endoscope is a signal to start recording a video image of the subject, and the issued identification information is a management identification for managing the video image of the subject.

10. An endoscopic device that generates first DICOM information based on first information related to a subject and first additional information necessary for generating DICOM (Digital Imaging and Communication in Medicine)-format data of the first information, the medical device comprising:

a first transmitter/receiver configured to receive second information generated by an ultrasonic observation device and second additional information from the ultrasonic observation device via a network defined by a prescribed protocol different from a DICOM protocol, the ultrasonic observation device compares the first information to the second information, and determines a segment of data of the second information that is different than the first information based on the comparison between the first information and the second information, the first information being an endoscope image and the second information being an ultrasonic image, the first transmitter/receiver receives only the segment of data of the second information and the second additional information from the ultrasonic observation device using the prescribed protocol different from the DICOM protocol; and a processor programmed to generate first DICOM information based on the first information and the first additional information, and generate second DICOM information based on the second information and the second additional information received from the ultrasonic observation device via the first transmitter/receiver; and a second transmitter/receiver configured to transmit the first DICOM information and the second DICOM information to a DICOM server via a network that is defined by the DICOM protocol.

11. A medical communication system comprising:

an endoscopic device including:

a memory storing first additional information to be added to first information related to a subject, the first information being an endoscope image, a processor programmed to generate DICOM (Digital Imaging and Communication in Medicine)-format data of the first information, a first transmitter/receiver, and a second transmitter/receiver; and an ultrasonic observation device configured to store second additional information to be added to second information related to the subject, the second information being an ultrasonic image, wherein:

the first transmitter/receiver is configured to communicate the second information and at least a portion of the second additional information stored in the ultrasonic observation device between the endoscopic device and the ultrasonic observation device via a network defined by a prescribed protocol different from a DICOM protocol;

the processor is programmed to generate DICOM-format data of the second information based on at least the second information and the second additional information received via the first transmitter/receiver;

the ultrasonic observation device (i) compares the first information to the second information, and determines a segment of data of the second information that is different than the first information based on the comparison between the first information and the second information, and (ii) transmits only the segment of data of the second information and the second additional information to the first transmitter/receiver of the endoscopic device using the prescribed protocol different from the DICOM protocol; and the second transmitter/receiver is configured to transmit generated DICOM-format data of the first information and generated DICOM-format data of the second information to a DICOM server via a network defined by the DICOM protocol.

* * * * *